(12) United States Patent
MacPherson et al.

(10) Patent No.: US 6,958,364 B1
(45) Date of Patent: Oct. 25, 2005

(54) USE OF FISCHER-TROPSCH CONDENSATE AS A LEAN OIL FOR HEAVY ENDS RECOVERY FROM FISCHER-TROPSCH TAIL GAS

(75) Inventors: Stuart R. MacPherson, Sunninghill (GB); Simon Clarke, Berkshire (GB)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 10/956,670

(22) Filed: Oct. 1, 2004

Related U.S. Application Data

(60) Provisional application No. 60/588,919, filed on Jul. 15, 2004.

(51) Int. Cl.⁷ .......................... C07C 27/00; B01D 19/00
(52) U.S. Cl. ...................... 518/728; 518/700; 95/158; 95/159
(58) Field of Search ............................. 518/700, 728; 95/158, 159

(56) References Cited

U.S. PATENT DOCUMENTS

| | | | |
|---|---|---|---|
| 2,577,634 A | * | 12/1951 | Scharmann ................ 518/722 |
| 6,015,450 A | | 1/2000 | Joshi et al. |
| 6,709,569 B2 | | 3/2004 | Moore, Jr. et al. |

FOREIGN PATENT DOCUMENTS

| | | |
|---|---|---|
| WO | WO 02/14242 A1 | 2/2002 |
| WO | WO 02/14763 A1 | 2/2002 |

OTHER PUBLICATIONS

C. Judson King, "Separation Processes", McGraw-Hill, Inc. 1971, pp. 347-350.
R. N. Maddox, "Gas Absorption" in "'Chemical Engineers' Handbook", McGraw-Hill, Inc. 1973, Section 14, p. 14-2.

* cited by examiner

*Primary Examiner*—J. Parsa
(74) *Attorney, Agent, or Firm*—James W. Ambrosius

(57) ABSTRACT

A process for recovering light Fischer-Tropsch hydrocarbons from a rich tail gas produced from a Fischer-Tropsch synthesis operation which comprises: (a) recovering separately from a Fischer-Tropsch synthesis operation a Fischer-Tropsch condensate and a hydrocarbon rich Fischer-Tropsch tail gas; (b) cooling the Fischer-Tropsch condensate and Fischer-Tropsch tail gas; (c) using the cooled Fischer-Tropsch condensate as a lean oil to adsorb at least a portion of the light Fischer-Tropsch hydrocarbons present in the Fischer-Tropsch tail gas, whereby a rich oil mixture comprising Fischer-Tropsch condensate and light Fischer-Tropsch hydrocarbons is formed; and (d) collecting the rich oil mixture.

12 Claims, 1 Drawing Sheet

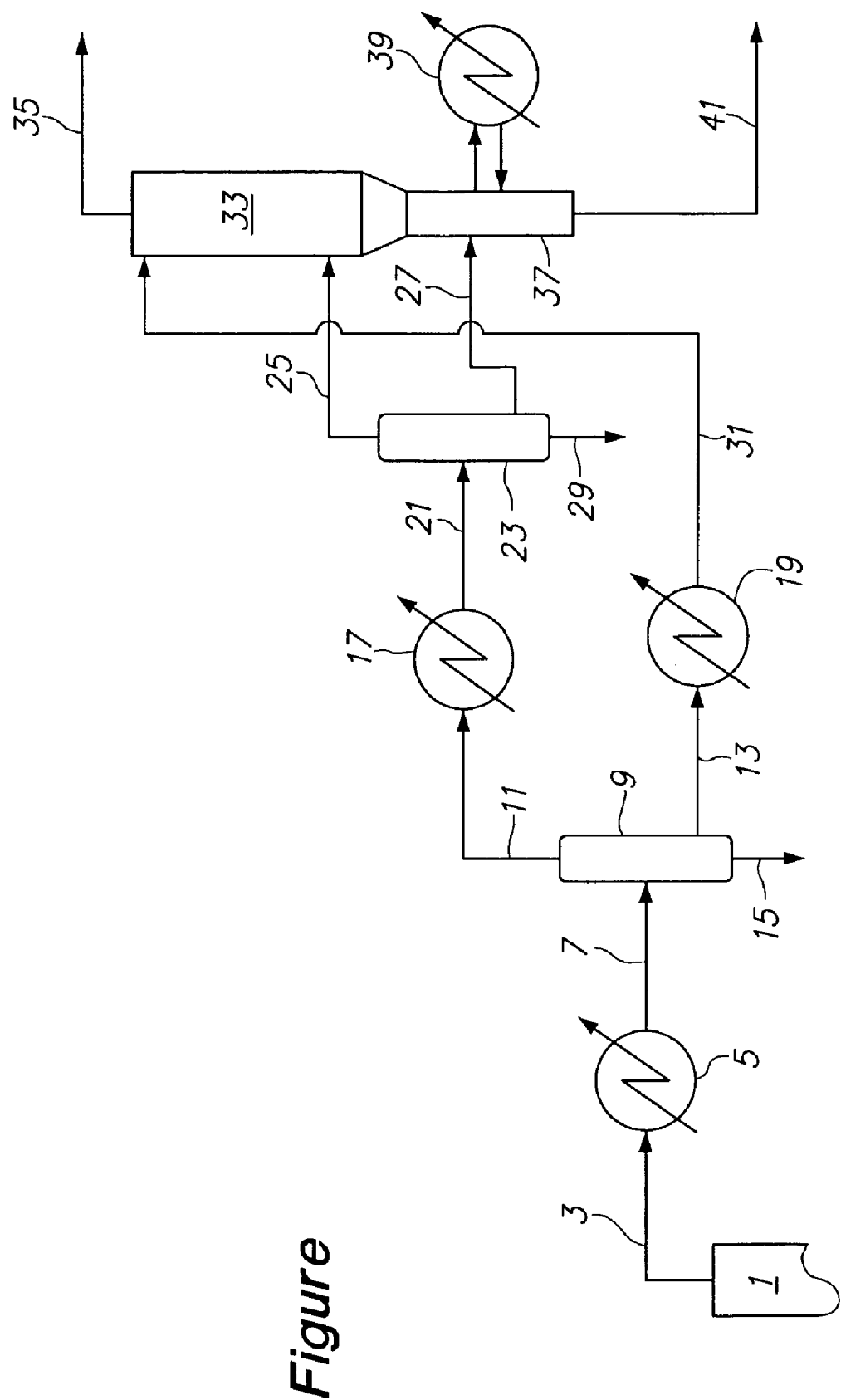
*Figure*

USE OF FISCHER-TROPSCH CONDENSATE AS A LEAN OIL FOR HEAVY ENDS RECOVERY FROM FISCHER-TROPSCH TAIL GAS

CROSS REFERENCE TO RELATED APPLICATION

This application claims priority from U.S. Provisional Application No. 60/588,919 filed Jul. 15, 2004.

FIELD OF THE INVENTION

This invention relates to the use of Fischer-Tropsch condensate as lean oil for recovering the heavy hydrocarbons present in Fischer-Tropsch tail gas.

BACKGROUND OF THE INVENTION

Fischer-Tropsch synthesis operations produce hydrocarbons having a wide range of molecular weights. In general, Fischer-Tropsch hydrocarbons as recovered from the Fischer-Tropsch reactor may be divided up into three categories based roughly upon their boiling ranges. However, it should be understood that there is considerable overlap between the individual boiling ranges of each of the three categories. The heaviest fraction includes hydrocarbons boiling above about 680° F. and generally is referred to as Fischer-Tropsch wax. Fischer-Tropsch wax is usually solid at ambient temperature. An intermediate fraction boiling between ambient temperature and about 700° F. is referred to as condensate. The condensate fraction is a liquid at ambient temperature and contains hydrocarbons boiling within the range of naphtha and diesel. The lightest fraction is normally gaseous at ambient temperature and contains light hydrocarbons, i.e., hydrocarbons containing less than about five carbon atoms. Tail gas which represents an overhead product from the Fischer-Tropsch synthesis operation contains the light hydrocarbon fraction plus carbon oxides, hydrogen, and water vapor. Tail gas is generally considered a low value product which may be recycled to the reactor or burned locally as fuel. Although much of the hydrocarbons present in the tail gas are low value hydrocarbons, such as methane, ethane, and propane, the tail gas will also contain significant amounts of butane and propane, as well as some hexane, pentane, and octane. These $C_4$ to $C_8$ hydrocarbons represent commercially valuable products which it would be desirable to recover from the tail gas if an economically attractive means to do so is available. Unfortunately, there are few economically attractive methods for recovering these heavy ends from the tail gas.

Two conventional approaches are available for recovering the heavy ends from the tail gas. Cryogenic cooling may be used to condense and remove the heavy ends from Fischer-Tropsch tail gas. A second approach is to use a circulating lean oil in an adsorption tower to adsorb the hydrocarbons in the tail gas to form rich oil. However, conventional lean oil recovery methods require a regeneration loop where the valuable hydrocarbon products are extracted from the rich oil prior to re-circulating the regenerated lean oil back to the adsorption tower.

The present invention is directed to an integrated process for recovering the heavy ends present in the Fischer-Tropsch tail gas by using the Fischer-Tropsch condensate fraction as a once through lean oil to adsorb the commercially valuable hydrocarbons. The process of the present invention does not require a regeneration loop because the Fischer-Tropsch condensate is not re-circulated. When combined with a stripper, the present process provides an integrated and efficient process for economically recovering the most valuable hydrocarbons from the tail gas while also removing carbon oxides, i.e., carbon dioxide and carbon monoxide, which are also present and are known to cause problems in downstream hydroprocessing operations.

As used in this disclosure the words "comprises" or "comprising" are intended as open-ended transitions meaning the inclusion of the named elements, but not necessarily excluding other unnamed elements. The phrases "consists essentially of" or "consisting essentially of" are intended to mean the exclusion of other elements of any essential significance to the composition. The phrases "consisting of" or "consists of" are intended as a transition meaning the exclusion of all but the recited elements with the exception of only minor traces of impurities.

SUMMARY OF THE INVENTION

The present invention is directed to a process for recovering light Fischer-Tropsch hydrocarbons from a hydrocarbon rich tail gas produced from a Fischer-Tropsch synthesis operation which comprises (a) recovering separately from a Fischer-Tropsch synthesis operation a Fischer-Tropsch condensate and a hydrocarbon rich Fischer-Tropsch tail gas; (b) cooling the Fischer-Tropsch condensate and Fischer-Tropsch tail gas; (c) using the cooled Fischer-Tropsch condensate as a lean oil to adsorb at least a portion of the light Fischer-Tropsch hydrocarbons present in the Fischer-Tropsch tail gas, whereby a rich oil mixture comprising Fischer-Tropsch condensate and light Fischer-Tropsch hydrocarbons is formed; and (d) collecting the rich oil mixture.

The Fischer-Tropsch hydrocarbon rich tail gas as recovered from the Fischer-Tropsch synthesis operation comprises methane, $C_2$ to about $C_8$ hydrocarbons, carbon oxides, hydrogen, and water vapor. The Fischer-Tropsch condensate comprises mostly $C_5$ to about $C_{19}$ hydrocarbons with both lighter and heavier hydrocarbons also being present in lesser amounts. Generally, the hydrocarbon rich tail gas and the condensate are recovered as overhead from the Fischer-Tropsch reactor and are subsequently separated into normally liquid and normally gaseous fractions. Both the gaseous Fischer-Tropsch hydrocarbon rich tail gas and the liquid Fischer-Tropsch condensate are preferably cooled to a temperature conducive to the adsorption of the heavy ends present in the tail gas, i.e., hydrocarbons containing about four or more carbon atoms. The adsorption of the $C_4$ plus Fischer-Tropsch hydrocarbons into the condensate preferably takes place in an adsorption column in which the Fischer-Tropsch hydrocarbon rich tail gas and the condensate are introduced in countercurrent flow relative to one another. The pressure in the adsorption column should be sufficient to facilitate the adsorption of most of the $C_4$ plus hydrocarbons and some of the $C_3$ hydrocarbons present in the tail gas into the condensate which serves as the lean oil. Preferably, the Fischer-Tropsch condensate and Fischer-Tropsch tail gas are introduced into the adsorption column at a temperature and pressure pre-selected to result in the adsorption of at least about 50 wt % of the propane and substantially all of the pentane present in the rich Fischer-Tropsch tail gas.

In one embodiment of the invention, the rich oil mixture comprising the Fischer-Tropsch condensate and adsorbed light Fischer-Tropsch hydrocarbons recovered from the tail gas pass to a stripper which is operated at a temperature and pressure sufficient to remove those hydrocarbons having an end boiling point below a pre-selected temperature. Preferably, the stripper is operated at a temperature and pressure so that the product effluent from the stripper, referred to in this disclosure as the second rich oil mixture, contains at least 80 wt % of the pentane that was originally present in the rich oil mixture recovered from the adsorption column. Preferably as much of the propane and butane are recovered as is practical while removing most of the carbon oxides that are adsorbed in the rich oil mixture.

BRIEF DESCRIPTION OF THE DRAWING

The drawing is a schematic representation showing one embodiment of the process that is the present invention.

DETAILED DESCRIPTION OF THE INVENTION

The drawing illustrates a simplified schematic diagram which may be used to illustrate features of the invention. A hot vapor mixture at a temperature of about 200° C. comprising tail gas and condensate is collected in line 3 as overhead from the Fischer-Tropsch reactor 1. The overhead is cooled to about 70° C. in a first heat exchanger 5 and passed via line 7 to a first separator 9 where the overhead is separated into a hydrocarbon rich tail gas 11, Fischer-Tropsch condensate 13, and water 15. Both the hydrocarbon rich tail gas and the Fischer-Tropsch condensate are further cooled to about 5° C. by tail gas heat exchanger 17 and condensate heat exchanger 19, respectively. The cooled tail gas from the tail gas heat exchanger 17 is sent by line 21 to a second separator 23 where it is further separated into a chilled rich tail gas 25, a tail gas condensate 27, and a second water stream 29. The chilled condensate from condensate heat exchanger 19 collected in line 31 serves as the lean oil and is carried to the top of the adsorption column 33 where it will flow downward in countercurrent flow to the chilled rich tail gas which has been introduced via line 25 into the bottom of the adsorption column. Under the temperature and pressure conditions maintained in the adsorption column most of the $C_4$ and $C_5$ hydrocarbons and much of the $C_3$ minus hydrocarbons as well as some carbon dioxide and carbon monoxide are adsorbed by the lean oil which is now referred as rich oil. Of course, any $C_6$ plus hydrocarbons present in the hydrocarbon rich tail gas will be preferentially adsorbed by the lean oil as well. The rich oil is mixed in the bottom of the adsorption column with tail gas condensate entering via line 27. A lean tail gas comprising primarily hydrogen, carbon oxides, methane, and ethane exits the top of the adsorption column by line 35. The rich oil mixture passes into the stripping section 37 of the adsorption column where it is passed through a reboiler 39 where some of the light hydrocarbons, mostly propane and some butane, and most of the carbon oxides are stripped out. The stripped rich oil consisting essentially of $C_3$ plus hydrocarbons is collected in line 41. The light hydrocarbons and carbon oxides removed in the stripper pass out of the top of the adsorption column with the lean tail gas 35. The rich oil mixture is generally sent by line 41 to further upgrading operations, such as hydrotreating or dewaxing.

Typical compositions of the various streams in the drawing are shown in the Table below:

TABLE

| Stream Number | 11 | 13 | 31 | 25 | 27 | 35 | 41 |
|---|---|---|---|---|---|---|---|
| Stream Description | Rich Tail Gas | Light HC Condensate | Lean Oil | Cooled Rich Tail Gas | Tail Gas Condensate | Lean Tail Gas | Stripped Rich Oil |
| Temperature, Deg. C. | 70 | 70 | 5 | 5 | 5 | 10 | 240 |
| Pressure, barg | 20 | 20 | 22 | 18 | 22 | 17 | 18 |

TABLE-continued

| Stream Number | 11 | 13 | 31 | 25 | 27 | 35 | 41 |
|---|---|---|---|---|---|---|---|
| Components (mol/hr.)* | | | | | | | |
| Water | 142 | 6 | 6 | 4 | 1 | 9 | |
| Hydrogen | 2395 | 2 | 2 | 2395 | | 2397 | |
| Carbon Monoxide | 2187 | 4 | 4 | 2186 | 0.5 | 2190 | |
| Carbon Dioxide | 3152 | 23 | 23 | 3134 | 9 | 3165 | |
| Methane | 2161 | 5 | 5 | 1259 | 1 | 1265 | |
| Ethane | 44 | 0.6 | 0.6 | 43 | 0.5 | 44 | |
| Propane | 23 | 1 | 1 | 22 | 1 | 21 | 3 |
| N-Butane | 24 | 2 | 2 | 20 | 4 | 13 | 13 |
| N-Pentane | 22 | 5 | 5 | 12 | 9 | 4 | 23 |
| N-Hexane | 16 | 10 | 10 | 4 | 12 | 2 | 24 |
| C7 | 11 | 19 | 19 | 1 | 10 | 1 | 29 |
| C8 | 6 | 19 | 19 | | 5 | | 25 |
| C9 | 3 | 22 | 22 | | 3 | | 25 |
| C10 | 1 | 23 | 23 | | | | 25 |

*Numbers shown are representative only of the typical components present in each of the streams.

It will be noted that the hydrocarbon rich tail gas, line 11 in the drawing, recovered from the first separator 9 contains significant amounts of $C_2$ to $C_5$ hydrocarbons and carbon oxides, as well as diminishing amounts of hexane, heptane, octane, nonane, and decane. The most commercially valuable hydrocarbons are the $C_5$ plus hydrocarbons. Therefore, it should be noted that some propane, much of the n-butane, and most of the $C_5$ plus hydrocarbons are captured in the effluent (line 41 in the drawing) from the adsorption column/stripper. Also, it is important to note that substantially all of the carbon oxides are absent from line 41 and are instead recovered in the lean tail gas (line 35 in the drawing). The lean tail gas may be further processed or burned as fuel.

Typical operating conditions for the adsorption column and the stripper are also shown in the Table. The adsorption column is usually operated so that the lean oil captures most of the $C_3$ to $C_5$ hydrocarbons present in the Fischer-Tropsch tail gas. By cooling the hydrocarbon rich tail gas and the condensate to at least about 5° C. prior to introduction into the adsorption column the majority of the $C_5$ plus hydrocarbons present in the tail gas will be captured along with some of the $C_3$ and $C_4$ hydrocarbons. In the stripper, the temperature and pressure should be sufficient to remove substantially all of the carbon oxides from the rich oil in order to facilitate the downstream upgrading operations. Preferably as much of the propane and butane as practical will be recovered from the adsorption column.

While the process of the present invention may be used with other types of Fischer-Tropsch reactors, it is especially advantageous to use the process of the invention with a slurry-type reactor. In a slurry-type reactor, the condensate and hydrocarbon rich tail gas are recovered separately from the high molecular weight waxy fraction. Thus the condensate and the hydrocarbon rich tail gas mixture may be readily separated into its components in a separator as is illustrated in the drawing.

What is claimed is:

1. A process for recovering light Fischer-Tropsch hydrocarbons from a rich tail gas produced from a Fischer-Tropsch synthesis operation which comprises:
   (a) recovering separately from a Fischer-Tropsch synthesis operation a Fischer-Tropsch condensate and a hydrocarbon rich Fischer-Tropsch tail gas;
   (b) cooling the Fischer-Tropsch condensate and Fischer-Tropsch tail gas;

(c) using the cooled Fischer-Tropsch condensate as a lean oil to adsorb at least a portion of the light Fischer-Tropsch hydrocarbons present in the Fischer-Tropsch tail gas, whereby a rich oil mixture comprising Fischer-Tropsch condensate and light Fischer-Tropsch hydrocarbons is formed; and (d) collecting the rich oil mixture.

2. The process of claim 1 wherein the cooled Fischer-Tropsch condensate and cooled Fischer-Tropsch tail gas are introduced in step (c) into an adsorption column in countercurrent flow relative to one another.

3. The process of claim 2 including the additional steps of (i) passing the rich oil mixture from step (c) comprising the Fischer-Tropsch condensate and the light Fischer-Tropsch hydrocarbons through a stripper wherein substantially all of the carbon oxides present are removed from the rich oil mixture and (ii) collecting prior to step (d) a second rich oil mixture from the stripper comprising the Fischer-Tropsch condensate and those light Fischer-Tropsch hydrocarbons falling within a pre-selected boiling range.

4. The process of claim 3 wherein the rich Fischer-Tropsch tail gas comprises Fischer-Tropsch $C_2$ to $C_5$ hydrocarbons and carbon oxides.

5. The process of claim 4 wherein the rich oil mixture comprises Fischer-Tropsch condensate and $C_3$ to $C_5$ Fischer-Tropsch hydrocarbons adsorbed from the hydrocarbon rich Fischer-Tropsch tail gas.

6. The process of claim 5 wherein the second rich oil mixture comprises Fischer-Tropsch condensate and $C_4$ and $C_5$ Fischer-Tropsch hydrocarbons.

7. The process of claim 5 wherein the Fischer-Tropsch condensate and Fischer-Tropsch tail gas are introduced into the adsorption column at a temperature and pressure preselected to result in the adsorption of at least about 50 wt % of the propane and substantially all of the pentane present in the rich Fischer-Tropsch tail gas.

8. The process of claim 7 wherein the stripper is operated at a temperature and pressure so that the second rich oil mixture contains at least 80 wt % of the pentane that was present in the rich oil mixture of step (c).

9. The process of claim 2 wherein the Fischer-Tropsch condensate and Fischer-Tropsch tail gas are cooled to at least about 5° C. prior to introduction into the adsorption column.

10. The process of claim 3 wherein the lower section of the adsorption column contains the stripper.

11. The process of claim 3 wherein the second rich oil mixture is sent to an up-grading operation.

12. The process of claim 1 wherein the Fischer-Tropsch synthesis reaction is carried out in a slurry-type reactor.

* * * * *